United States Patent
Coleman et al.

(10) Patent No.: US 10,407,460 B2
(45) Date of Patent: Sep. 10, 2019

(54) SOLID PHASE SEQUENCE-INDEPENDENT NUCLEIC ACID ASSEMBLY

(71) Applicant: The Regents of the University of California, Oakland, CA (US)

(72) Inventors: Todd Prentice Coleman, La Jolla, CA (US); Phillip Kyriakakis, La Jolla, CA (US)

(73) Assignee: The Regents of the University of Califonia, Oakland, CA (US)

( * ) Notice: Subject to any disclaimer, the term of this patent is extended or adjusted under 35 U.S.C. 154(b) by 0 days.

(21) Appl. No.: 15/572,428

(22) PCT Filed: May 9, 2016

(86) PCT No.: PCT/US2016/031532
§ 371 (c)(1),
(2) Date: Nov. 7, 2017

(87) PCT Pub. No.: WO2016/179602
PCT Pub. Date: Nov. 10, 2016

(65) Prior Publication Data
US 2018/0134747 A1    May 17, 2018

Related U.S. Application Data

(60) Provisional application No. 62/158,425, filed on May 7, 2015.

(51) Int. Cl.
| | | |
|---|---|---|
| *C07H 21/04* | (2006.01) | |
| *C07H 21/02* | (2006.01) | |
| *C12M 1/34* | (2006.01) | |
| *C12Q 1/6844* | (2018.01) | |
| *C12M 1/00* | (2006.01) | |
| *C07H 1/00* | (2006.01) | |
| *C07H 21/00* | (2006.01) | |

(52) U.S. Cl.
CPC .............. *C07H 21/04* (2013.01); *C07H 1/00* (2013.01); *C07H 21/00* (2013.01); *C07H 21/02* (2013.01); *C12M 1/00* (2013.01); *C12M 1/34* (2013.01); *C12Q 1/6844* (2013.01); *C12Q 2533/107* (2013.01); *C12Q 2565/543* (2013.01)

(58) Field of Classification Search
CPC .......... C07H 21/04; C07H 21/02; C12M 1/34; C12Q 1/6844; C12Q 2533/107; C12Q 2565/543
USPC ........................................ 435/91.2; 536/25.3
See application file for complete search history.

(56) References Cited

U.S. PATENT DOCUMENTS

| | | |
|---|---|---|
| 6,372,429 B1 | 4/2002 | Sharon |
| 8,507,226 B2 | 8/2013 | Carr et al. |
| 2003/0228602 A1 | 12/2003 | Parker et al. |
| 2005/0048514 A1 | 3/2005 | Bennett et al. |
| 2011/0092380 A1* | 4/2011 | Stahler ................ B01J 19/0046 506/9 |
| 2014/0187447 A1 | 7/2014 | Kucera et al. |

OTHER PUBLICATIONS de Raad et al. A Solid-Phase Platform for Combinatorial and Scarless Multipart Gene Assembly. ACS Synth. Biol. 2013, 2, 316-326 (Year: 2013).*
De Koning et al., "Repetitive elements may comprise over two-thirds of the human genome", PLoS genetics, 2011, 7(12), e1002384.
Eroshenko et al., "Gene Assembly from Chip-Synthesized Oligonucleotides", Current protocols in chemical biology, 2012, pp. 1-17.
Gibson et al., "Enzymatic assembly of DNA molecules up to several hundred kilobases", Nature methods, 2009, 6(5), pp. 343-345.
Hoffmann et al., "Solid-phase PCR in a picowell array for immobilizing and arraying 100000 PCR products to a microscope slide", Lab on a Chip, 2012, 12(17), pp. 3049-3054.
Kaiser et al., "Template-Directed Synthesis in 3'-and 5'-Direction with Reversible Termination", Angewandte Chemie International Edition, 2012, 51(33), pp. 8299-8303.
Kim et al., "'Shotgun DNA synthesis' for the high-throughput construction of large DNA molecules", Nucleic acids research, 2012, gks546.
Kok et al., "Rapid and reliable DNA assembly via ligase cycling reaction", ACS synthetic biology, 2014, 3(2), pp. 97-106.
Kosuri et al., "Large-scale de novo DNA synthesis: technologies and applications", Nature methods, 2014, 11(5), pp. 499-507.
Lee et al., "A high-throughput optomechanical retrieval method for sequence-verified clonal DNA from the NGS platform", Nature communications, 2015, 6.
Ma et al., "DNA synthesis, assembly and applications in synthetic biology", Current opinion in chemical biology, 2012, 16(3), pp. 260-267.
Quan et al., "Parallel on-chip gene synthesis and application to optimization of protein expression", Nature biotechnology, 2011, 29(5), pp. 449-452.
International Search Report and Written Opinion for PCT Application No. PCT/US2016/031532, dated Aug. 16, 2016, 9 pages.

* cited by examiner

*Primary Examiner* — Yih-Horng Shiao
(74) *Attorney, Agent, or Firm* — Perkins Coie LLP

(57) ABSTRACT

Disclosed herein are methods of assembling nucleic acid fragments, such as non overlapping nucleic acid fragments, in an orientation-specific, sequence-independent way. The methods entail annealing one or more nucleic acid fragments to be assembled onto a solid phase via matching barcodes having sequences complementary to the solid phase oligos, ligating the nucleic acid fragments by end-to-end ligation, and recovering the ligated nucleic acid from the solid phase.

24 Claims, 7 Drawing Sheets

SOLID PHASE SEQUENCE-INDEPENDENT NUCLEIC ACID ASSEMBLY

CROSS-REFERENCE TO RELATED APPLICATIONS

This patent document is a 35 U.S.C. § 371 National Stage application of International Application No. PCT/US2016/031532 entitled "SOLID PHASE SEQUENCE-INDEPENDENT NUCLEIC ACID ASSEMBLY" filed May 9, 2016 which claims benefit of priority of U.S. Provisional Patent Application No. 62/158,425, entitled "SOLID PHASE SEQUENCE-INDEPENDENT OLIGONUCLEOTIDE ASSEMBLY" filed on May 7, 2015. The entire content of the aforementioned patent applications are incorporated by reference as part of the disclosure of this patent document.

TECHNICAL FIELD

This patent document relates to systems, devices, and processes for assembling nucleic acid fragments on a solid phase.

BACKGROUND

This patent document relates to assembling nucleic acid fragments, particularly fragments that are difficult to be assembled using conventional technology. In general, it is challenging to synthesize large nucleic acids in one step due to the error rate of incorporating each additional nucleotide. Therefore, large size nucleic acids are assembled from smaller fragments that can be sequence verified. It is difficult to assemble certain sequences, such as sequences containing small fragments that do not have overlapping sequences or sequences containing many repeats. The technology disclosed herein solves these problems by providing a method to assemble nucleic acids in an orientation-specific, sequence-independent way on a solid phase.

SUMMARY

Examples of implementations of the disclosed technology can be used to provide systems, devices and techniques for assembling nucleic acids such as polynucleotides and oligonucleotides in a way that is independent of sequence. The disclosed technology can be used to assemble nucleic acids sequentially, enabling the assembly of large nucleic acid sequences, including repetitive sequences. Some exemplary large nucleic acid sequences include but are not limited to DNA, RNA, locked nucleic acid (LNA), unlocked nucleic acid (UNA) and other nucleic acids. The disclosed technology for assembling nucleic acids can be used in various applications including a personal nucleic acid printer, a large scale gene synthesis platform and nucleic acids for materials, such as nanoparticles.

In one aspect, the disclosure relates to a method of assembling nucleic acid fragments. The method entails the steps of: (a) annealing a first nucleic acid fragment to a first solid phase oligo bound to a solid phase; (b) annealing a second nucleic acid fragment to a second solid phase oligo bound to the solid phase to cause the first nucleic acid fragment and the second nucleic acid fragment to ligate to each other; (c) ligating the first nucleic acid fragment and the second nucleic acid fragment by end-to-end ligation; and (d) cleaving the ligated nucleic acid at a position close to the junction of the second nucleic acid fragment and the second solid phase oligo to obtain an assembled nucleic acid comprising the first nucleic acid fragment and the second nucleic acid fragment, wherein the assembled nucleic acid remains annealed to the first solid phase oligo.

In some embodiments, the first nucleic acid fragment and the second nucleic acid fragment are non-overlapping. In some embodiments, steps (b)-(d) are repeated to assemble one or more additional nucleic acid fragments. In some embodiments, steps (a) and (b) are carried out sequentially in any order or simultaneously. The nucleic acid fragments to be assembled can be single-stranded or double-stranded. In some embodiments, the first nucleic acid fragment comprises a first barcode at the 3' end, and the second nucleic acid fragment comprises a second barcode at the 5' end. The first bar code can bind to the first solid phase oligo, and the second bar code can bind to the second solid phase oligo. The barcodes can be completely complementary or partially complementary to the corresponding solid phase oligos. When the barcodes are partially complementary to the corresponding solid phase oligos, one barcode can bind to one or more solid phase oligos; or one solid phase oligo can bind to one or more barcodes.

The method can further entail a polymerization step such that one or more single-stranded nucleic acid fragments are polymerized into double-stranded nucleic acid fragments. The polymerization step can be performed before, after, or during the ligation step.

The method further entails a step to recover the assembled nucleic acid from the solid phase. The recovery step can be performed by cleaving the assembled nucleic acid, amplifying the assembled nucleic acid, or any other method disclosed herein.

In another aspect, disclosed herein is a system for assembling nucleic acid fragments. The system comprises a solid phase comprising two or more solid phase oligos bound to the solid phase; two or more nucleic acid fragments to be assembled, wherein each nucleic acid fragment comprises a barcode which is complementary to one or more solid phase oligos, wherein when the two or more nucleic acid fragments are in contact with the solid phase, the nucleic acid fragments are immobilized on the solid phase via the annealing between the barcodes and the solid phase oligos, such that the nucleic acid fragments are capable of being ligated to each other by end-to-end ligation.

In one aspect, a method of assembling nucleic acids such as polynucleotides and oligonucleotides includes assembling non-overlapping nucleic acid fragments, each containing a barcode that is complimentary to an oligo which is covalently linked to a solid phase (solid phase oligo). These nucleic acid fragments are brought into proximity by annealing to the solid phase oligos and then ligated end-to-end. The barcodes on the nucleic acid fragments to be assembled can be fully complimentary to the solid phase oligos or may contain mismatches as long as the barcodes can bind to the solid phase oligos. Assembling non-overlapping nucleic acid fragments using end-to-end ligation can include annealing a first nucleic acid fragment with a first barcode and a second nucleic acid fragment with a second barcode. The first and second barcodes can have different melting temperatures. In some embodiments, a plurality of nucleic acid fragments to be assembled can anneal to the solid phase simultaneously.

In another aspect, a method of assembling nucleic acids includes obtaining nucleic acid fragments including a first nucleic acid fragment barcoded with a first barcode and a second nucleic acid fragment barcoded with a second barcode. The first and second barcodes are barcodes that immobilize nucleic acid fragments by binding to the solid phase oligos via annealing. The method includes adding the first nucleic acid fragment onto a surface to anneal to a solid phase oligo and become immobilized onto the surface. The method includes enabling a polymerase, such as a DNA polymerase, to use the immobilized first nucleic acid fragment as a primer to turn the first nucleic acid fragment into a double stranded nucleic acid. The method includes annealing the second nucleic acid fragment onto the surface via binding to the second solid phase oligo. The method includes ligating the annealed second nucleic acid fragment to the double stranded first nucleic acid. The method includes enabling another polymerization such that the second nucleic acid fragment is turned into a double-stranded nucleic acid.

In some embodiments, the method disclosed herein includes annealing both nucleic acid fragments to be assembled simultaneously. As a result, this method can include polymerizing both nucleic acid strands simultaneously prior to ligation. This method can include using an additional primer to polymerize fragment one or fragment two. Alternatively, this method can also include ligation of the two single-stranded nucleic acid fragments prior to polymerization. Nucleic acid fragments to be assembled can be added to the solid phase by annealing in any order.

The method can be implemented in various ways to include one or more of the following features. For example, the method can include assembling one or more additional nucleic acid fragments. Controlling orientation of the nucleic acid fragments can be through design of the sequence and orientation of the barcodes and the solid phase oligos.

The method includes cleaving the ligated double stranded nucleic acid with a nuclease specific to cutting on or after the second barcode to obtain ligated double-stranded first and second nucleic acid fragments and a smaller nucleic acid reverse compliment of the solid phase nucleic acid. The method includes selectively removal of the smaller nucleic acid left over after cutting. Recovering the assembled nucleic acid includes cleaving with nucleases specific to the first or second barcode to obtain a fully assembled double-stranded nucleic acid. The method can include amplifying the assembled nucleic acid from the surface using strand displacement amplification (SDA). The method can include amplifying the assembled nucleic acid off of the surface by polymerase chain reaction (PCR). The method can include recovering the assembled nucleic acids by melting thermally or by chemical methods. The method can include assembling a barcoded plasmid backbone or other single or double stranded nucleic acids.

In another aspect, a nucleic acid or gene printer is configured to perform operations of the disclosed methods. The nucleic acid printer can be configured to print ready-to-use plasmids. The nucleic acid printer can be configured to print ready-to-use nucleic acid materials.

In another aspect, a nucleic acid or gene printer is configured to perform operations of the disclosed methods.

In another aspect, a chip device such as a semiconductor chip is configured to perform operations of the disclosed method. The semiconductor chip device can be implemented in various ways to include one or more of the following features. For example, the semiconductor chip device can include one area or one address on the chip that contains fully assembled nucleic acid; and other areas or addresses on the chip contain not fully assembled nucleic acid. The semiconductor chip device can include microarrays with immobilized and barcoded solid phase oligos. The semiconductor chip device can include sequencing flow cells or microfluidics. The semiconductor chip device can include microarrays having a mixture of nucleic acid fragments annealed to specific locations on the microarrays in parallel, and assembled in parallel. The semiconductor chip device can be configured to generate large libraries of nucleic acid sequence variants.

In another aspect, an inkjet nucleic acid printer is configured to perform operations of the disclosed methods to spot reagents for assembly of nucleic acid fragments on a plate. The inkjet nucleic acid printer can be implemented in various ways to include one or more of the following features. For example, the inkjet nucleic acid printer can be configured to enable nucleic acid recovery through aspiration. The inkjet nucleic acid printer can be configured to receive a desired nucleic acid sequence; and print the nucleic acid sequence as linear nucleic acids, as double stranded nucleic acids, or be taken from the solid phase in a way that forms more complex structures. The inkjet nucleic acid printer can be configured to ligate the printed linear nucleic acid fragments into circular nucleic acids, such as double stranded plasmid DNA or a circular single stranded nucleic acid.

In other aspects, methods, systems, and devices can be implemented for assembling nucleic acids using end-to-end ligation according to the disclosed technology.

BRIEF DESCRIPTION OF THE DRAWINGS

FIG. 3A shows single-stranded nucleic acids are annealed to solid phase oligos. FIG. 3B shows direct ligation of single-stranded nucleic acids. FIG. 3C shows one single-stranded nucleic acid is polymerized into double-stranded nucleic acid and then ligated with another single-stranded nucleic acid. FIG. 3D shows both single-stranded nucleic acids are polymerized into double-stranded nucleic acids and then ligated.

DETAILED DESCRIPTION

Figure 1A:
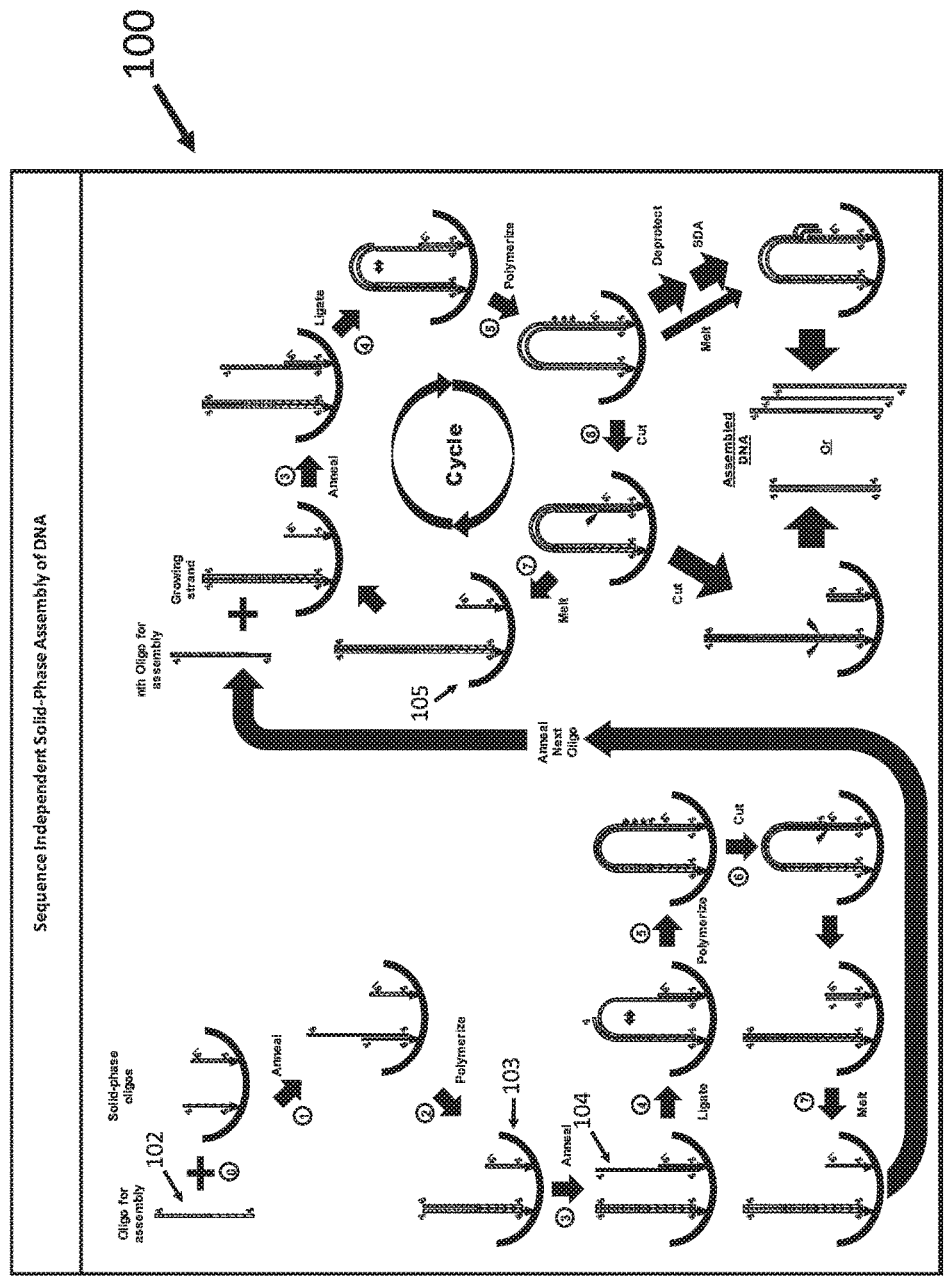
FIG. 1A is a diagram showing an exemplary process for assembling oligonucleotides according to the disclosed technology.

Synthesizing large nucleic acids can be accomplished by assembling smaller nucleic acid fragments that contain overlapping sequence. For example, overlapping sequences can be annealed and each nucleic acid to be assembled can be used as a primer to polymerize the overlapping nucleic acids, fusing them together by PCR or Gibson assembly etc. This conventional assembly method relies on the ability to generate unique overlapping sequences and sequences that are favorable to annealing at a specific condition (e.g., temperature, pH, salt concentration, etc.). In addition, when assembling more than two fragments, several unique overlapping sequences that anneal under the same conditions (temperature, pH, salt concentration etc.) need to be found. Assembling nucleic acid fragments using unique overlapping sequences may not work well in assembling repetitive sequences due to the requirement of unique overlapping sequences. Also, the assembly reaction is done in solution, limiting its scalability. Moreover, assembling nucleic acid fragments using unique overlapping sequences cannot always accurately predict how the nucleic acid fragments being assembled will anneal, especially when assembling large numbers of nucleic acid fragments. This can lead to failure in assembly reactions, which requires a redesign and synthesis of the nucleic acid fragments and their overlaps. Some sequences may not even be amiable to this process and require assembly through cloning several small fragments into a plasmid or genome one at a time. These constraints can lead to an approach to assemble by assembling several partial sequences, followed by a second, third (or more) cloning steps, usually after an initial attempt has failed. This can be very time consuming, requiring up to several weeks to obtain a desired sequence.

The technology disclosed herein largely avoids the limitations of the process of assembling nucleic acid fragments that require overlapping sequences. First, the disclosed technology is sequence-independent and does not depend on the nucleic acid fragments being assembled to have any overlapping sequence. Thus, the disclosed technology can be used to assemble repetitive sequences, or sequences with either unusually high or low G/C or A/T content. Moreover, because the assembly chemistry is "solid phase" the disclosed technology can be achieved "on chip" with minor modifications of off the shelf technologies. Thus, the disclosed technology is highly scalable to assembling thousands or millions of nucleic acid fragments such as polynucleotides and oligonucleotides in parallel.

The ability to assemble nucleic acid fragments in a sequence-independent manner has important implications on synthetic biology, a growing field in academia and industry. Synthetic and systems biology approaches often require systematically changing sequences in order to optimize or study some biological system. It is common that these changes are repetitive patterns of nucleic acid sequence, for example, testing the effects on copy number of nucleic acid binding sites on transcription or copies on amino acid sequences on binding strength. Yet, when current art is tested for failure rate, they are tested against random sequences or variants of a particular gene that does not contain repetitive elements. In addition, the synthetic biology field aims at bottom up approaches to making synthetic organisms/genomes, yet 51-78% of the mammalian genome consists of "repetitive sequences" (this does not even include the aforementioned repetitive patterns that can influence gene promoter strength or copy number etc.). While current technologies promise to deliver synthesis and assembly of thousands of unique nucleic acid sequences, they are fundamentally limited in their ability to assemble nucleic acids that are commonly desired in biology and synthetic biology. There is no existing technology that can assemble multiple nucleic acid fragments in an orientation specific manner that does not rely on overlapping nucleic acid sequences.

The disclosed technology works by assembling nucleic acids through end-to-end ligation, eliminating the need for overlapping fragments, yet has the ability to control the order of assembly. End-to-end ligation eliminates the sequence dependence of the two nucleic acid fragments being assembled as a factor for assembly. There is more than one way to achieve sequence-independent assembly once the one or more nucleic acid fragments to be assembled are immobilized on a solid phase. The disclosed technology includes several variations that can provide various advantages for specific applications. The disclosed technology accomplishes this by using barcoded nucleic acid fragments, which fragments are immobilized to a surface by complementary binding between the barcodes and the solid phase oligos. The orientation of the nucleic acid fragments to be assembled is determined by synthesizing or attaching the barcodes on the 5' end or the 3' end of the nucleic acid fragments. The area where the nucleic acid is assembled will have two solid phase oligos linked to the surface, one attached by the 5' end and the other attached to the 3' end to the solid phase. In some embodiments, both solid phase oligos are attached to the solid phase by the 5' end. In some embodiments, both solid phase oligos are attached to the solid phase by the 3' end.

Solid Phase Oligos

The method disclosed herein includes the use of solid phase oligos bound to a solid phase through covalent coupling using carboxylic acids, primary naliphatic amines, aromatic amines, choromethyls (vinyl benzyl chloride), amides, hydrazides, aldehydes, hydroxyls, thiols, epoxys, disulfides groups, carbonyl amides, thioureas, sulfonamides, carboxamides or other linkage chemistries. In some embodiments, the oligos are bound to the solid phase via photoactivatable or photocleavable linkages. For example, photocleavable linkages that selectively cleave the first or second solid phase oligo can be used. In some embodiments, the solid phase oligos or the nucleic acids to be assembled can have certain modifications, such as phosphates, fluorophores, fluorescent quenchers, spacers, phosphoorthate bonds, dideoxynucleic acids, biotin, or cap analogs (5'-5' Dinucleoside Triphosphates).

The solid phase oligos have various sequences that are complementary to the sequences of the barcodes attached to the end of the nucleic acid fragments to be assembled. In some embodiments, the solid phase oligos have sequences that are completely complementary to the barcodes. In other embodiments, the solid phase oligos have sequences that are partially complementary to the barcodes. For example, the sequence of a solid phase oligo can have a mismatch to the sequence of the matching or corresponding barcode, as long as the barcode can still bind to the solid phase oligo and be immobilized on the solid phase. It is within the purview of one of ordinary skill in the art to select suitable sequences for the barcodes and the solid phase oligos.

Figure 1B:
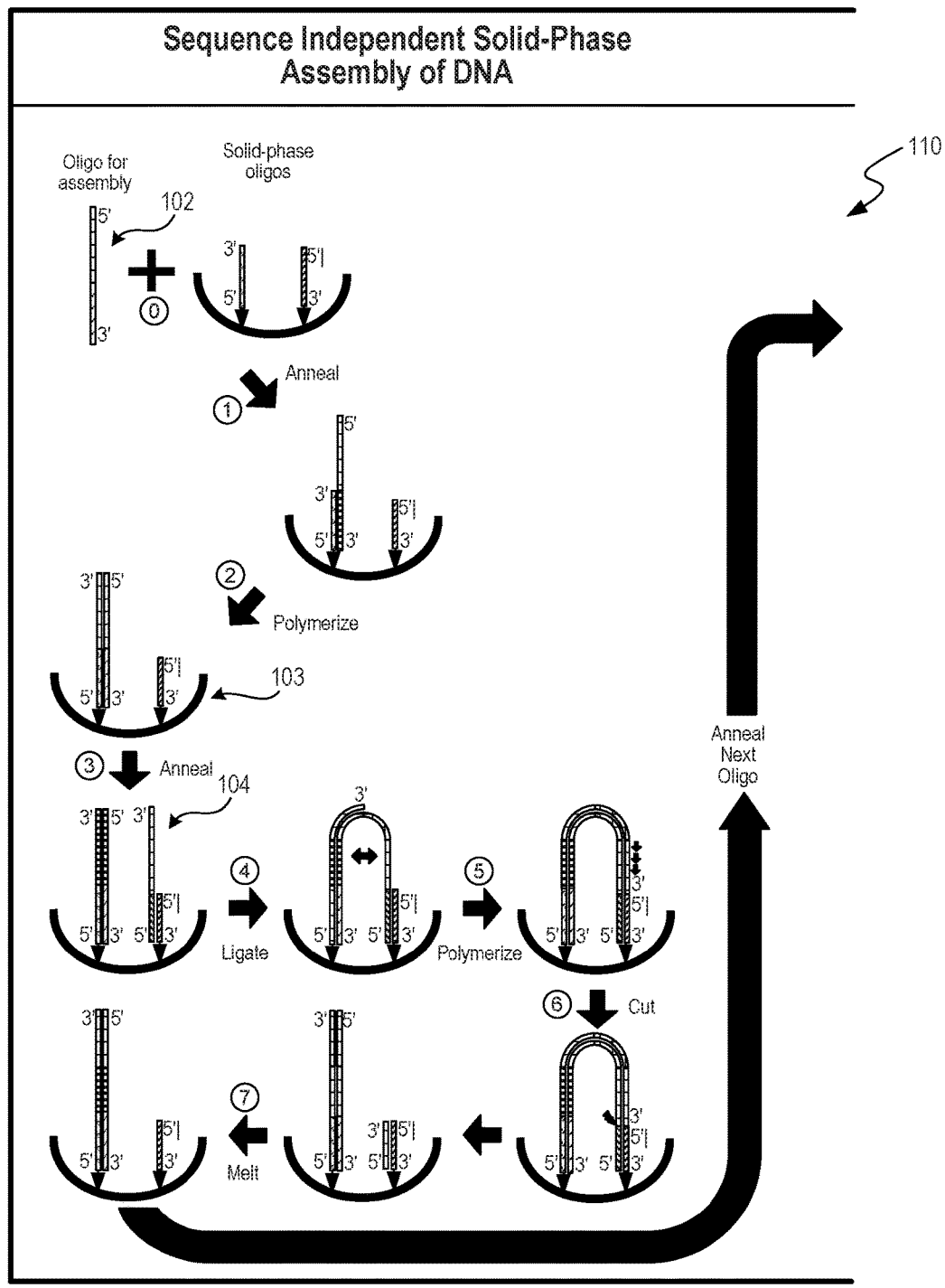
FIGS. 1B and 1C are enlarged two halves of the diagram in FIG. 1A.
Figure 1C:
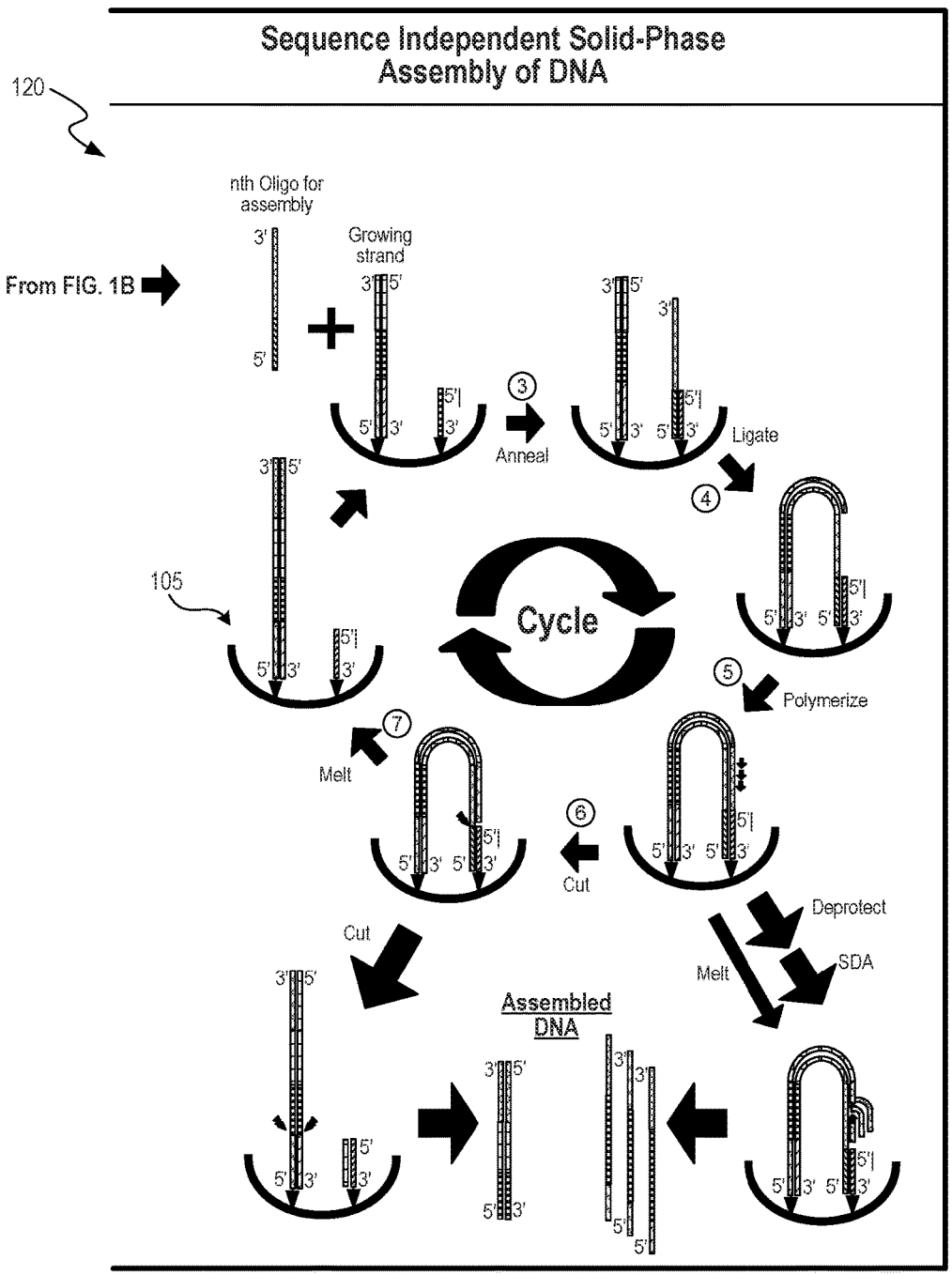
Figure 2A:
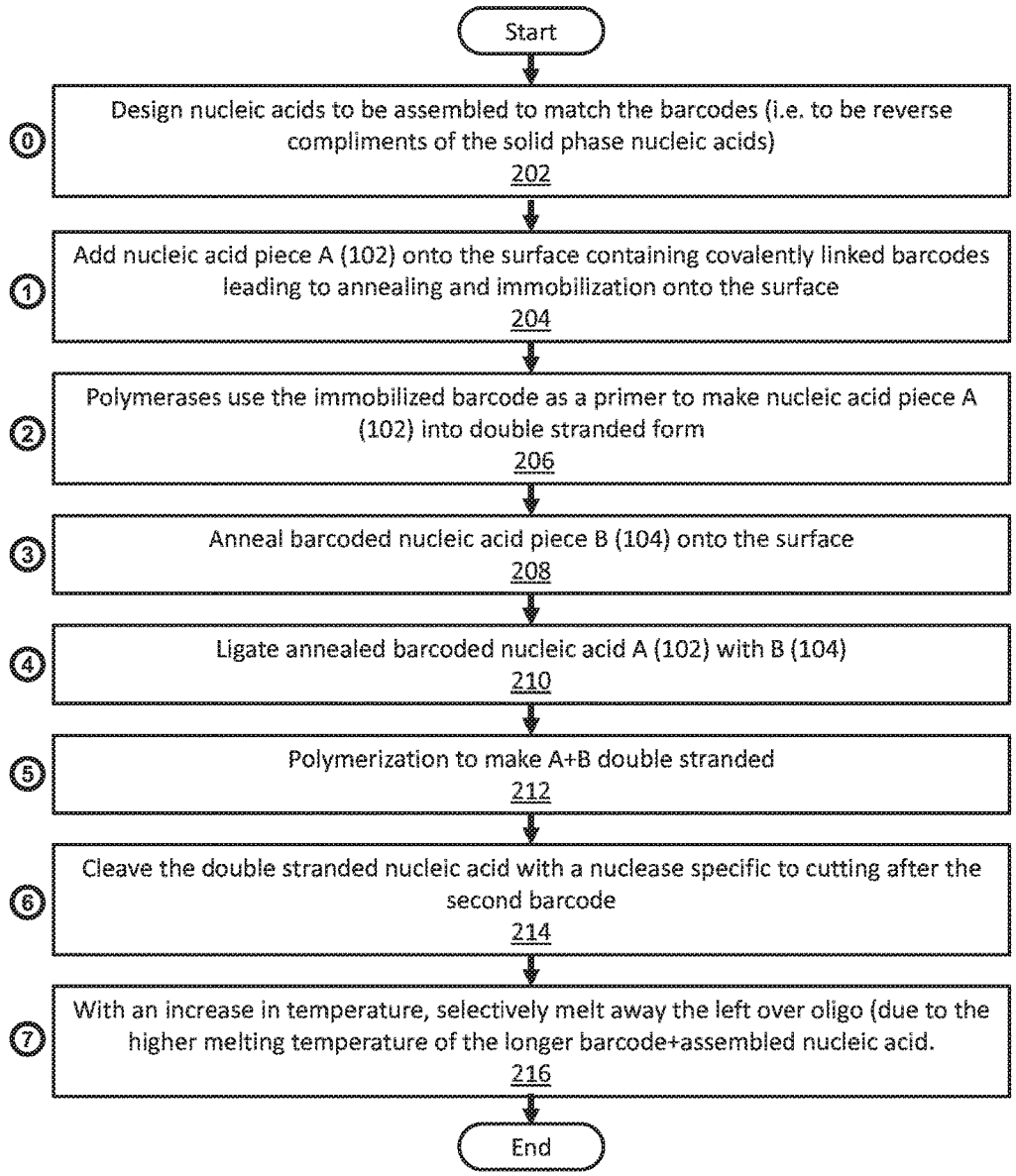
FIGS. 2A and 2B are exemplary process flow diagrams showing a process for assembling oligonucleotides.
Figure 2B:
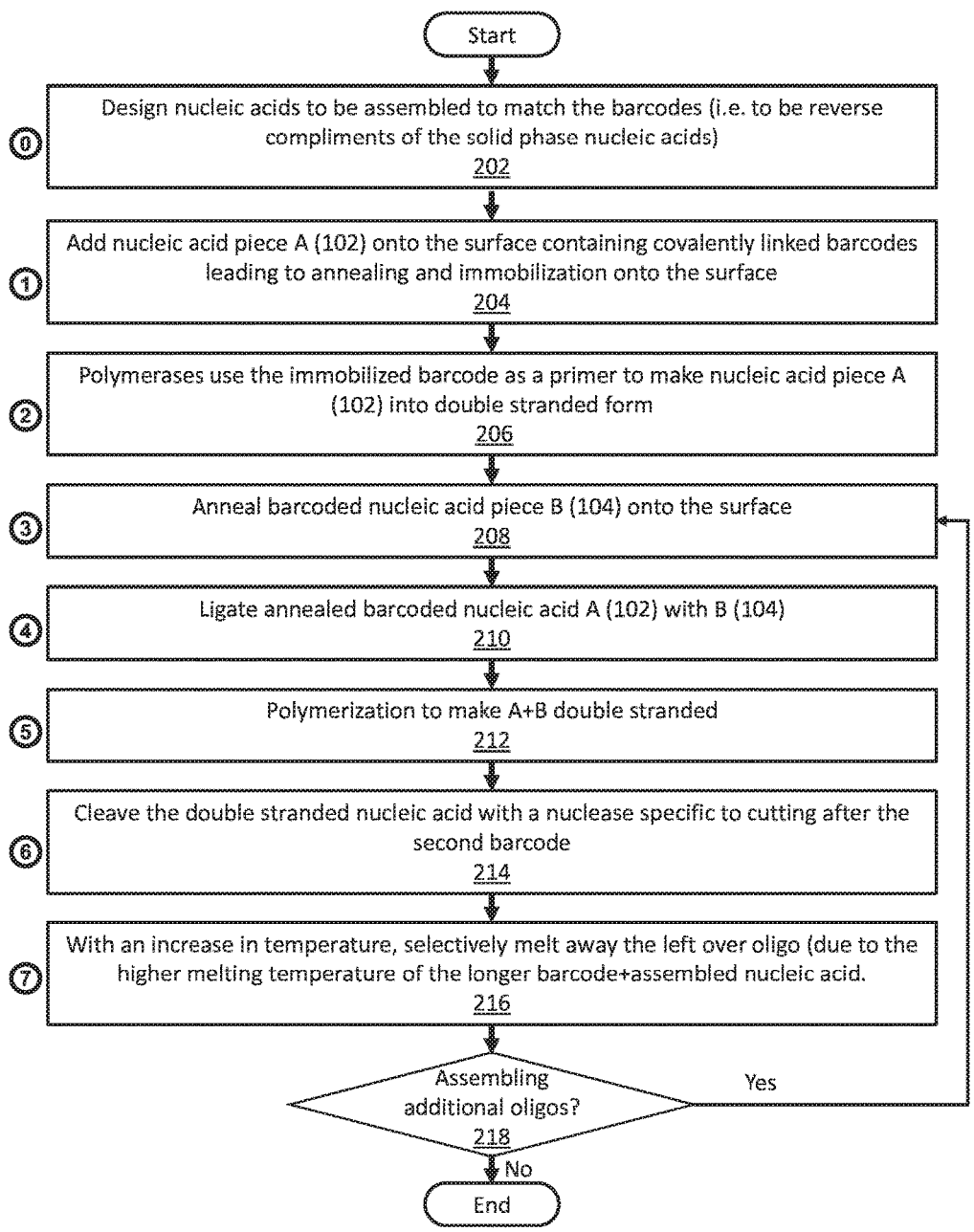

FIG. 1A is a diagram 100 showing a process for assembling nucleic acid fragments according to the disclosed technology. FIGS. 1B and 1C are enlarged two halves 110 and 120 of the diagram 100 in FIG. 1A. FIGS. 2A and 2B are process flow diagrams showing a process 200 for assembling nucleic acid fragments. The process 200 show in flow diagram format the process shown in FIGS. 1A, 1B, and 1C. Reference numbers 1 through 10 embedded in circles as shown in FIGS. 1A, 1B, and 1C match the individual processes in the flow diagram shown in FIGS. 2A and 2B. The following paragraphs are described with respect to FIGS. 1A, 1B, 1C, 2A, and 2B.

Nucleic acid fragments to be assembled should be designed to match (i.e., to be reverse complimentary to) the solid phase oligos (202). For example, when one desires "nucleic acid fragment A" (102) to be assembled with "nucleic acid fragment B" (104), "nucleic acid fragment A" (102) will be phosphorylated and barcoded with the reverse compliment of a longer solid phase oligo and "nucleic acid fragment B" will be barcoded with the reverse compliment of a shorter solid phase oligo. The longer solid phase oligo can have a higher melting temperature whereas the shorter solid phase oligo will have a lower melting temperature. In some embodiments, both solid phase oligos can have the same melting temperature. Since the orientation of the nucleic acid fragments to be assembled is controlled by the corresponding barcode sequences and the orientation of the barcodes, the nucleic acid fragments are ligated specifically in the desired orientation.

Nucleic acid fragment A (102) is added onto the surface containing the solid phase oligos covalently linked to the surface, leading to annealing and immobilizing of nucleic acid fragment A (102) onto the surface (204). Nucleic acid polymerases use the immobilized nucleic acid fragment as a primer to turn "nucleic acid fragment A" into a double-stranded nucleic acid fragment (206). Barcoded "nucleic acid fragment B" (104) is annealed onto the surface (208) and ligated to "nucleic acid fragment A" (210), followed by another polymerization step (212). Next, the nicked double-stranded nucleic acid is cleaved with a nuclease specific to cutting near the second solid phase oligo (214) leaving behind double-stranded nucleic acid A (102)+B (104) and a small barcode complimentary to shorter solid phase oligo. With a change in the chemical or physical environment (e.g., an increase in temperature, change in pH or salt concentration, etc.) the smaller barcode is then selectively melted away and the longer barcode and the assembled nucleic acid remains on the solid phase due to the higher melting temperature thereof (216). The smaller barcode can also be removed by the addition of another nucleic acid with a higher binding strength than the barcode.

The diagram associated with process (216) in FIG. 2 and (103) in FIGS. 1A, 1B, and 1C resemble the diagram after process (206) in FIGS. 2A, 2B and (105) in FIGS. 1A, 1B, and 1C. Thus, the process described above can be repeated in multiple cycles to assemble additional nucleic acid fragments onto the nucleic acid remaining immobilized on the solid phase. When additional nucleic acid fragments are desired to be assembled (218), the process 200 repeats starting process (208) in FIGS. 2A and 2B and (3) in FIGS. 1A, 1B, and 1C. The right half of FIG. 1A (i.e., FIG. 1C) shows how an arbitrary number of nucleic acid fragments can be added onto the growing strand of immobilized nucleic acid by repeating processes (208) through (216) as shown in FIGS. 2A and 2B or processes (3) through as shown in FIGS. 1A, 1B, and 1C.

Nucleic Acid Fragments to be Assembled

Figure 3:
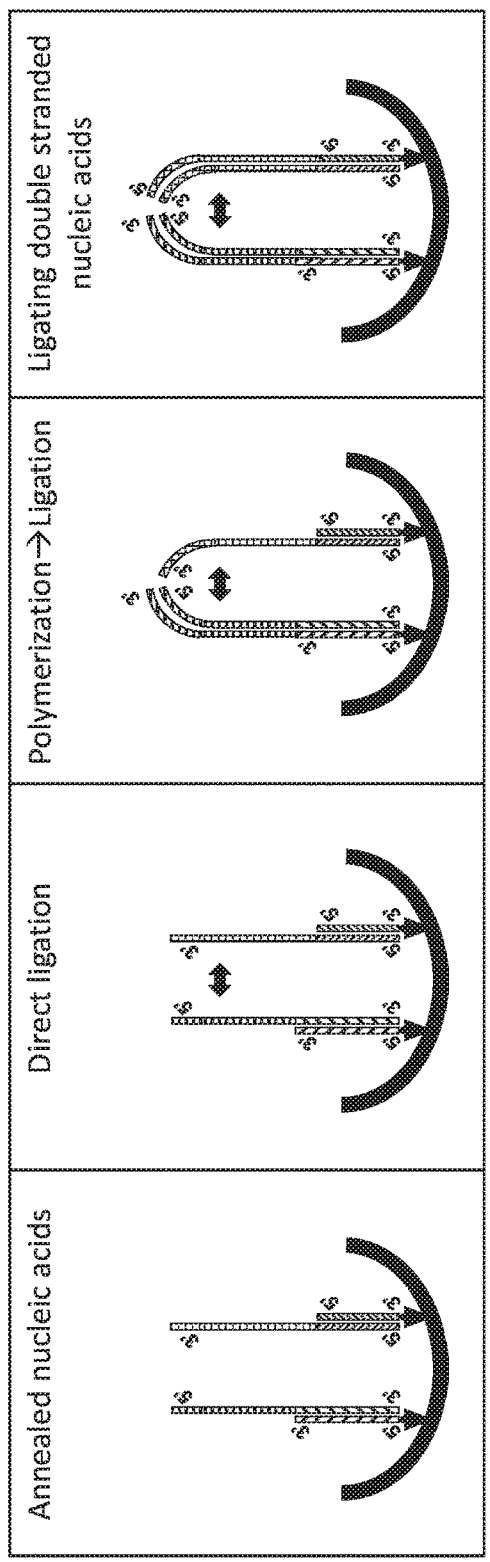
FIG. 3 exemplifies different embodiments of ligation and polymerization. For example, single-stranded nucleic acids can be ligated before or after polymerization into double-stranded nucleic acids.

In some embodiments, nucleic acid fragments to be assembled can be single stranded (FIGS. 3A and 3B) or double stranded (FIG. 3D) or a combination of double-stranded and single-stranded (FIG. 3C). The double-stranded nucleic acid fragment can have a sticky end with part or all of a barcode complimentary to the matching solid phase oligo. The double-stranded nucleic acids to be assembled can be a cut plasmid. The plasmid can be made partially single-stranded by an endonuclease or exonuclease or by ligating a single-stranded nucleic acid to the cut plasmid prior to annealing onto the solid phase. Similarly, the double-stranded nucleic acids to be assembled can be a genomic DNA or a double-stranded RNA. Ligation can be performed between two single-stranded nucleic acid fragments (FIGS. 3A and 3B) or two double-stranded nucleic acid fragments (FIG. 3D). Alternatively, ligation can be performed between a single-stranded nucleic acid fragment and double-stranded nucleic acid fragment (FIG. 3C). Nucleic acid fragments to be assembled can be synthesized in vitro or in vivo.

In some embodiments, multiple nucleic acid fragments to be assembled are annealed to the solid phase oligos simultaneously. In other embodiments, the nucleic acid fragments to be assembled are annealed to the solid phase oligos sequentially or one-by-one after the previously annealed fragment is assembled.

In some embodiments, single-stranded nucleic acid fragments are ligated into one piece before polymerized into double-stranded nucleic acid. In other embodiments, single-stranded nucleic acid fragments are each polymerized into double-stranded nucleic acid fragments and then ligated. Alternatively, the ligation step and the polymerization step can be performed in any order or simultaneously such that a single-stranded nucleic acid fragment is ligated to a double-stranded nucleic acid fragment.

Barcode and Solid Phase Oligo Selection

Barcodes and solid phase oligos can be chosen based on the unique sequences or physical properties or a combination of the two. The barcode can be attached to either the 5' end or the 3' end of a nucleic acid fragment to be assembled. As illustrated in FIG. 1A, a barcode is attached to the 3' end of nucleic acid fragment 102, and another barcode is attached to the 5' end of nucleic acid fragment 104. The orientation of the nucleic acid fragments to be assembled is controlled by attaching the barcodes to different ends.

Barcodes should be unique, different in sequence from the nucleic acids to be assembled. If the source of nucleic acids to be assembled is a mixture of oligos, barcodes and solid phase oligos can be chosen to sort the oligos in the mixture by selective and/or specific binding to the solid phase oligos. Thus, this technology is capable of multiplexing nucleic acid assembly from a pool of nucleic acid fragments. This is accomplished by the fact that the mixture of the nucleic acid fragments will only bind onto the solid phase via the barcodes matching the corresponding solid phase oligos. Therefore, unbound nucleic acid fragments may be reused to bind to a different solid phase having a set of different solid phase oligos. Additionally, the pool of nucleic acid fragments may be incubated with a surface having discrete spots containing different sets of solid phase oligos. Thus, this process can be used to sort the nucleic acid fragments in the mixture because the nucleic acid fragments in the mixture will only anneal on the part of the surface that has matching solid phase oligos.

In some embodiments, barcodes can be designed to be completely complementary to the solid phase oligos or to have mismatches to the solid phase oligos. Therefore, the barcodes can be designed such that each nucleic acid fragment binds specifically to one solid phase oligo or, alternatively, each nucleic acid fragment can bind to multiple solid phase oligos or multiple nucleic acid fragments can bind to one solid phase oligo. The probability that the nucleic acid fragments to be assembled can be calculated by the percentage of the sequences matching the solid phase oligos.

The length of the solid phase oligos and the nucleic acid fragments to be assembled can be adjusted to melt/anneal at specific, different temperatures or conditions. Barcodes can be cut off from the assembled or partially assembled nucleic acid. Modified nucleic acids can be utilized to change the binding strength after binding. For example, a photolabile group can change the nucleic acid structure as to have more or fewer hydrogen bonds with the solid phase oligo. In some embodiments, the solid phase oligos have the same melting temperature. In other embodiments, the solid phase oligos have different melting temperatures so that specific parts can be selectively melted and washed off. Melting can be increased or decreased by changing the physical or chemical environment (e.g. by changing temperature, or by adding or removing salts or detergents, changing pH, etc.).

Recovery of Assembled Nucleic Acid

Once the nucleic acid is fully assembled there are several possible ways to recover the assembled nucleic acid. One way would be to simply cleave it off with a nuclease specific to the barcode and the solid phase oligo, leaving fully assembled double-stranded nucleic acid. Alternatively, the nucleic acid can be amplified directly from the chip using single loop-mediated isothermal amplification (LAMP). A nucleic acid to be assembled may be designed to have a hairpin or loop on the bar code to facilitate amplification. Alternatively, strand displacement amplification (SDA) can be used for amplification. Primers for SDA can be designed to anneal the solid phase oligos or anywhere in the assembled nucleic acid. In addition, primers can anneal to the barcode, the assembled nucleic acid or the overlap of the junction between the barcode and the assembled nucleic acid. The 5' end of the solid phase oligo may be protected to prevent polymerization or ligation at this site. Mismatches between the solid phase oligos and the nucleic acid fragments to be assembled at or near the junction can be used to improve primer binding for SDA, PCR or similar amplification methods. SDA may result in a larger yield due to amplification, but would lead to single-stranded nucleic acid. Moreover, single-stranded nucleic acids can be melted off by heating. In addition, assembled nucleic acids can be amplified by PCR (DNA), transcription (DNA/RNA) or reverse transcription (RNA/DNA). If a fully assembled and ready to use nucleic acid is desired, it may be possible to assemble a barcoded plasmid backbone in the last cycle. This can be accomplished by cutting the plasmid with a restriction enzyme that leaves an overhang which can anneal to the solid phase oligo or by chewing back a few bases to expose single-stranded DNA that can anneal to the solid phase oligo. Alternatively, the double-stranded plasmid can be melted, allowing it anneal to the solid phase oligo.

Each recovery method has specific advantages. For example, if one desires to recover DNA and immediately use for cloning into a plasmid (as in a "personal gene printer"), the reaction can be easily scaled to yield larger amounts of DNA (with a larger solid phase). The resulting double-stranded DNA can be digested with a restriction enzyme or used in one of many types of ligation independent or other cloning methods. This printer could in principle print ready-to-use plasmids. For example a plasmid backbone can be designed so that single-stranded DNA with a barcode can be amplified using SDA, making it linearized with a barcode on a specific 5' end for addition onto the solid phase. Thus, the printed DNA can be ligated to the backbone and made double stranded with DNA polymerase, which can even be circularized by ligation after release from the solid phase. This DNA is ready for transformation which only requires as little as about 1 pg-100 ng of plasmid DNA. However, it may be scaled up to produce micrograms, milligrams, grams, or kilograms of nucleic acids.

When the application is to generate thousands of different nucleic acid fragments "on-chip", the SDA recovery may be more optimal. This allows the reaction to be scaled down significantly since the recovery process is also an amplification step. It may even be further advantageous since the deprotection process may in theory be controlled by light. In this set up the light can selectively deprotect different areas of the chip thereby selectively recovering the assembled nucleic acid. One application for this approach can be that one area or one "address" on the chip may contain fully assembled nucleic acid, while the others may require more rounds of assembly. There may be other reasons to utilize this approach. Another variation of this approach include annealing oligos for "nucleic acid fragment A" (102) and "nucleic acid fragment B" at the same time followed by an ligation step, a polymerization step and a cleaving step that leaves behind double-stranded DNA on the longer oligo (the product of process 216 in FIGS. 2A and 2B, and process 7 in FIGS. 1A, 1B, and 1C). This method may however require an additional protection or deprotection or both processes for the other solid-phase nucleic acid.

As one of ordinary skill in the art can appreciate, the assembled nucleic acid can be recovered by various means. For example, the method disclosed herein can include recovery of the nucleic acid using mechanically, for example using sonication. The method can include recovery of the nucleic acid thermally by heating or optical absorption/excitation. The method can include recovery of the nucleic acid chemically by enzyme cutting or by using redox chemistry or other chemical methods. The method can include recovery of the nucleic acid biochemically, such as through biotin elution. The method can include recovery of the nucleic acid by using photolabile or thermolabile groups. The method can include recovery of the nucleic acid cutting off the bar codes or leaving them in place.

It should be appreciated that the nucleic acid to be assembled can be one type of nucleic acid, while the nucleic acid that is amplified or copied from the solid phase may be a different type of nucleic acid. For example, an assembled DNA can be reverse transcribed into an RNA. In addition, multiple rounds of amplification from the solid phase may be utilized.

Error Checking

Figure 4:
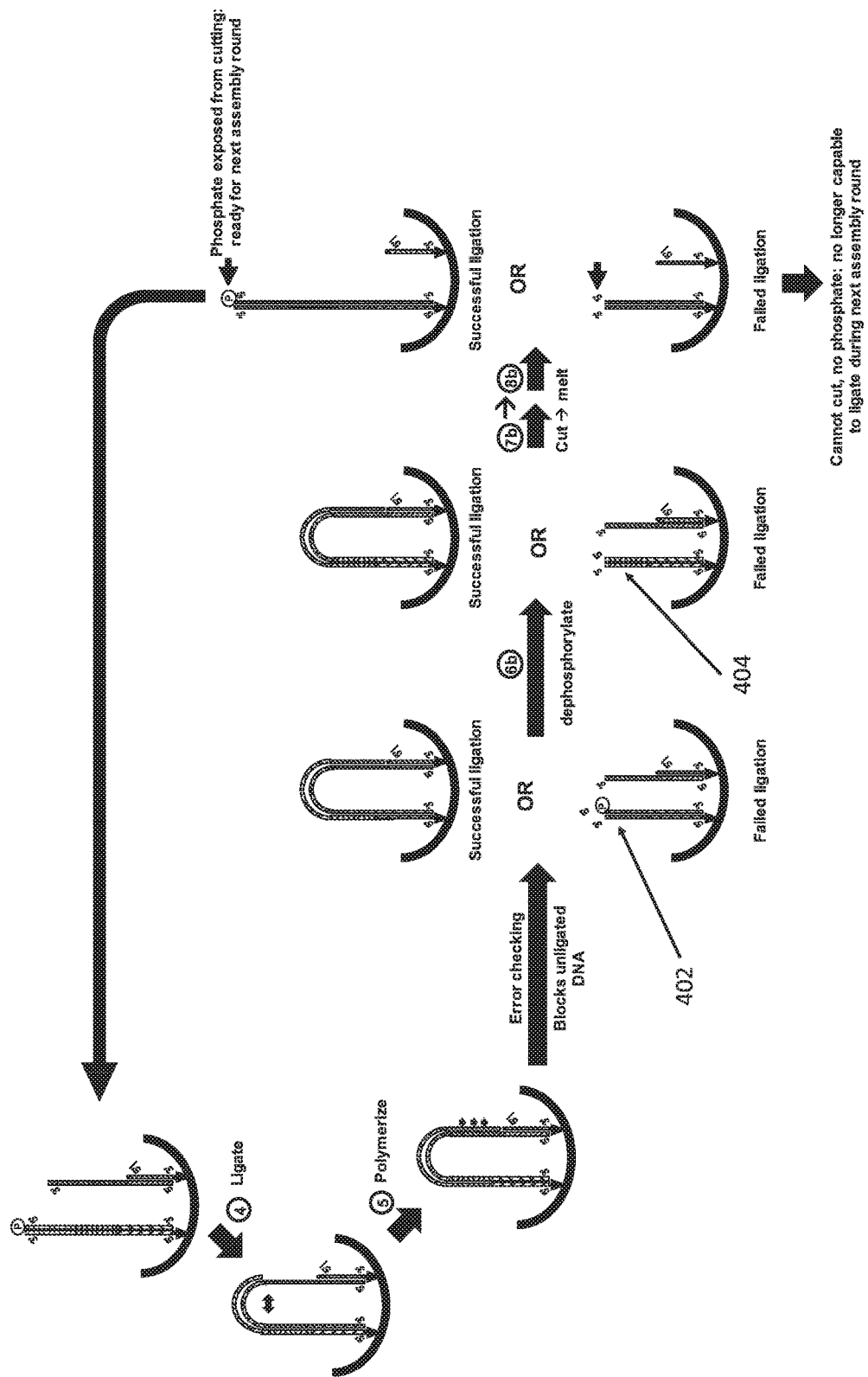
FIG. 4 exemplifies an error checking step. During the error checking step, nucleic acid fragments that failed to ligate are dephosphorylated such that these fragments are not capable to be ligated in the next round of assembly.

In some cases, "nucleic acid fragment A" (102) and "nucleic acid fragment B" (104) may fail to ligate (see FIGS. 1A and 1B and FIG. 4 (402)). The unligated nucleic acid fragment A may ligate to a subsequent nucleic acid fragment C making the assembled sequence A+C instead of A+B+C. Therefore, in some embodiments, an error prevention step may be included. As illustrated in FIG. 4, the failed ligation product (402) will contain an unused phosphate. A phosphatase may be used to remove this phosphate (494). Without the phosphate, it can no longer ligate to any additional nucleic acid fragment, blocking it from participating in future assembly rounds and ensuring that all growing strands will contain the correct sequence of assembled nucleic acids.

The design according to the disclosed technology would work well in a format for single gene assembly, making a nucleic acid/gene printer when combined with an oligosynthesizer. The disclosed technology could serve as a stand-alone device in a lab that prints desired nucleic acids. Furthermore, since all of the nucleic acid pieces are barcoded, the disclosed technology will also work in a "on-chip" format. In principle, one can immobilize the barcoded nucleic acids on a chip as with microarrays and sequencing flow cells/microfluidics. Then a mixture of oligos (potentially also made on-chip) can be annealed to specific locations on the array in parallel, and be assembled in parallel. Therefore, the disclosed technology enables the combined synthesis and assembly of tens, hundreds, thousands or even millions of nucleic acid fragments in parallel. Furthermore, it is possible to spot reagents for assembly of nucleic acid on the plate (using inkjet printing technology for example) instead of a purely microfluidics approach. Nucleic acid can then be recovered through aspiration. Thus, in addition to an assembly method that is independent of sequence, the disclosed technology also offers a more optimal strategy to dealing with the mixture of oligos produced by on-chip oligonucleotide synthesis ("array based oligo complexities") than current technologies (selective PCR amplification).

Exemplary Applications of the Disclosed Technology

The disclosed technology has many applications for synthesizing nucleic acids for sale to academia as well as industry. It is a large market and growing fast. There are two broad applications. One is to use the disclosed technology as part of a "personal nucleic acid synthesis machine", that would allow a user to enter a desired nucleic acid sequence and have it "printed". The entire plasmid can be designed from scratch; custom fit for the gene of interest, and can be "printed" as linear nucleic acid and even ligated by the nucleic acid printer into circular nucleic acids, such as plasmid DNA. The end user can then simply transform a custom plasmid; no other cloning steps would be necessary. The disclosed technology is a disruptive technology for the custom gene synthesis industry.

The second commercial application includes using the same concept, scaled up with an "on chip" design. This would enable the generation of thousands of long nucleic acid sequences or genes in parallel. This design could be used in a device that are favored by gene synthesis industry due to the high volume of production. This may be combined with a "on chip" synthesis of oligonucleotides—in a single device. In addition, this technology solves a major caveat to the "on chip" synthesis of oligonucleotides, how to manage the mixture of oligos that are synthesized. This technology addresses this since the oligos would bind the assembly chip based on their barcoded sequence. The disclosed technology can be applied for generating large libraries of nucleic acid sequence variants for understanding some biological phenomena or to optimize some biological process (e.g. optimizing an enzyme to improve bio-fuel production or an antibody to improve binding, etc.).

A third commercial application is for the synthesis of nucleic acids for materials, such as nanoparticles. A common feature of nucleic acids that can be programmed to be folded into complex structures/shapes (e.g., DNA/RNA origami) is that they contain repetitive sequences and/or sequences that form hairpins, duplexes, and other even more complex structures. These have uses in everything from novel surfaces, nanorobots, diagnostics, and medical treatments. Current nucleic acid assembly methods rely on assembling overlapping sequences, therefore may fail when the desired nucleic acids are specifically designed to be repetitive or have complex structures. This invention enables the assembly of single or double stranded nucleic acids, however, even double stranded nucleic acids can be amplified off the solid phase to convert it into a single strand by SDA or a similar method.

A fourth application is for the synthesis of nucleic acids for information or data storage. Nucleic acids can last millions of years and the ability to read them will not become obsolete as do human made technologies. Therefore, there is growing interest in using nucleic acids as a way to store information. However, in order to encode digital information it is highly desirable to be able to print any possible sequence. This invention assembles nucleic acids in a way that is sequence independent, therefore is ideal for assembling nucleic acids as information.

While this patent document contains many specifics, these should not be construed as limitations on the scope of any disclosed technology or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few embodiments are described. Other embodiments and their variations and enhancements can be made based on what is described and illustrated.

We claim:

1. A method of assembling nucleic acid fragments, comprising:
    (a) annealing a first nucleic acid fragment to a first solid phase oligonucleotide bound to a solid phase;
    (b) annealing a second nucleic acid fragment to a second solid phase oligonucleotide bound to the solid phase to prepare the first nucleic acid fragment and the second nucleic acid fragment for ligation to each other;
    (c) ligating the first nucleic acid fragment and the second nucleic acid fragment by end-to-end ligation; and
    (d) cleaving the ligated nucleic acid at a position close to the junction of the second nucleic acid fragment and the second solid phase oligonucleotide to obtain an assembled nucleic acid comprising the first nucleic acid fragment and the second nucleic acid fragment, wherein the assembled nucleic acid remains annealed to the first solid phase oligonucleotide,
    wherein the first or second solid phase oligonucleotide is used as a primer for polymerization to form double-stranded nucleic acids.

2. The method of claim 1, wherein the first nucleic acid fragment and the second nucleic acid fragment are non-overlapping.

3. The method of claim 1, wherein steps (b)-(d) are repeated to assemble one or more additional nucleic acid fragments.

4. The method of claim 1, wherein steps (a) and (b) are carried out sequentially or simultaneously.

5. The method of claim 1, wherein the first nucleic acid fragment comprises a first barcode at the 3' end, and the second nucleic acid fragment comprises a second barcode at the 5' end.

6. The method of claim 5, wherein the first bar code hybridizes to the first solid phase oligonucleotide, and the second bar code hybridizes to the second solid phase oligonucleotide.

7. The method of claim 6, wherein the first bar code is completely complementary to the first solid phase oligonucleotide.

8. The method of claim 6, wherein the first bar code is partially complementary to the first solid phase oligonucleotide.

9. The method of claim 6, wherein the second bar code is completely complementary to the second solid phase oligonucleotide.

10. The method of claim 6, wherein the second bar code is partially complementary to the second solid phase oligonucleotide.

11. The method of claim 1, wherein the first solid phase oligonucleotide and the second solid phase oligonucleotide are bound to the solid phase through covalent coupling.

12. The method of claim 1, further comprising cleaving the assembled nucleic acid from the solid phase at a position close to the junction of the first nucleic acid fragment and the first solid phase oligonucleotide.

13. The method of claim 5, wherein the first barcode and the second barcode have different melting temperatures.

14. The method of claim 1, wherein the first nucleic acid fragment is double-stranded.

15. The method of claim 14, wherein the first nucleic acid fragment has a sticky end which comprises the first barcode.

16. The method of claim 1, wherein the second nucleic acid fragment is double-stranded.

17. The method of claim 16, wherein the second nucleic acid fragment has a sticky end which comprises the second barcode.

18. The method of claim 1, wherein the first nucleic acid fragment is single-stranded, the second nucleic acid fragment is single-stranded, or both of the first and the second nucleic acid fragments are single-stranded.

19. The method of claim 18, further comprising, after step (a) and before step (b), polymerizing the first nucleic acid fragment to form a double-stranded first nucleic acid fragment.

20. The method of claim 18, further comprising, after step (b) and before step (c), polymerizing the second nucleic acid fragment to form a double-stranded second nucleic acid fragment.

21. The method of claim 18, further comprising, after step (c) and before step (d), polymerizing the ligated nucleic acid.

22. The method of claim 1, further comprising an error checking step, wherein an unligated nucleic acid fragment is dephosphorylated or blocked from further assembly.

23. The method of claim 1, further comprising recovering the assembled nucleic acid from the solid phase.

24. A system for assembling nucleic acid fragments, comprising:
a solid phase comprising two or more solid phase oligonucleotides bound to the solid phase, wherein the two or more solid phase oligonucleotides are used as primers for polymerization to form double-stranded nucleic acids;
two or more nucleic acid fragments to be assembled, wherein each nucleic acid fragment comprises a barcode which is complementary to one or more solid phase oligonucleotides,
wherein when the two or more nucleic acid fragments are in contact with the solid phase, the nucleic acid fragments are immobilized on the solid phase via the annealing between the barcodes and the solid phase oligonucleotides, such that the nucleic acid fragments are capable of being ligated to each other by end-to-end ligation.

* * * * *